US011164309B2

(12) United States Patent
Sati et al.

(10) Patent No.: US 11,164,309 B2
(45) Date of Patent: Nov. 2, 2021

(54) IMAGE ANALYSIS AND ANNOTATION

(71) Applicant: INTERNATIONAL BUSINESS MACHINES CORPORATION, Armonk, NY (US)

(72) Inventors: Marwan Sati, Mississauga (CA); David Richmond, Newton, MA (US)

(73) Assignee: International Business Machines Corporation, Armonk, NY (US)

(*) Notice: Subject to any disclaimer, the term of this patent is extended or adjusted under 35 U.S.C. 154(b) by 43 days.

(21) Appl. No.: 16/379,839

(22) Filed: Apr. 10, 2019

(65) Prior Publication Data
US 2020/0327659 A1    Oct. 15, 2020

(51) Int. Cl.
*G06K 9/00* (2006.01)
*G06T 7/00* (2017.01)
(Continued)

(52) U.S. Cl.
CPC .......... *G06T 7/0012* (2013.01); *G06K 9/4671* (2013.01); *G16H 30/40* (2018.01);
(Continued)

(58) Field of Classification Search
CPC ........ G06T 7/0012; G06T 2207/20072; G06T 2207/20081; G16H 70/60; G16H 50/20;
(Continued)

(56) References Cited

U.S. PATENT DOCUMENTS 6,058,322 A * 5/2000 Nishikawa ............ G06T 7/0012
600/408
8,311,310 B2 * 11/2012 Zhao ...................... G16H 50/20
382/133
(Continued)

FOREIGN PATENT DOCUMENTS

WO    2017151759 A1    9/2017

OTHER PUBLICATIONS

Mell et al., "The NIST Definition of Cloud Computing", Recommendations of the National Institute of Standards and Technology, Special Publication 800-145, Sep. 2011, 7 pages.

*Primary Examiner* — Tom Y Lu
(74) *Attorney, Agent, or Firm* — Dmitry Paskalov

(57) ABSTRACT

An embodiment of the invention may include a method, computer program product and computer system for object detection and identification. The method, computer program product and computer system may include computing device which may receive an image from an imaging device. The image may be a medical image. The computing device may detect one or more potential indicators of disease in the image using a first algorithm and determine areas of potential disease in the image using an artificial intelligence algorithm. The computing device may determine a correlation between the determined areas of potential disease in the image and the one or more potential indicators of disease for the image. The computing device may, in response to determining a positive correlation, identify one or more of the potential indicators of disease for annotation and generate a report indicating one or more potential indicators of disease was found in the image.

17 Claims, 8 Drawing Sheets

(51) Int. Cl.
  *G06K 9/46*     (2006.01)
  *G16H 50/20*    (2018.01)
  *G16H 30/40*    (2018.01)
  *G16H 70/60*    (2018.01)

(52) U.S. Cl.
  CPC ............. *G16H 50/20* (2018.01); *G16H 70/60* (2018.01); *G06K 2209/05* (2013.01); *G06T 2207/20072* (2013.01); *G06T 2207/20081* (2013.01)

(58) Field of Classification Search
  CPC ... G16H 30/40; G06K 9/4671; G06K 2209/05
  See application file for complete search history.

(56) References Cited

U.S. PATENT DOCUMENTS

| | | | |
|---|---|---|---|
| 9,589,374 B1* | 3/2017 | Gao | G06T 11/008 |
| 10,176,408 B2* | 1/2019 | Paik | G06K 9/6296 |
| 2017/0277841 A1* | 9/2017 | Shankar | G06F 19/00 |

* cited by examiner

IMAGE ANALYSIS AND ANNOTATION

BACKGROUND

The present invention relates generally to a method, system, and computer program for image analysis and annotation. More particularly, the present invention relates to a method, system, and computer program for analyzing medical images for disease and disease probability and annotating the medical images.

Medical imaging includes techniques and processes to create visual representations of the interior of a body for clinical analysis and medical intervention. Further, medical imaging seeks to provide a visual representation of the functions of some organs or tissues. Medical imaging also seeks to reveal internal structures which may be hidden by skin and/or bones, as well as to diagnose and treat disease. Medical imaging has allowed the medical community to establish a database of normal anatomy and physiology enabling the identification of physiological abnormalities including indicators of disease.

BRIEF SUMMARY

An embodiment of the invention may include a method, computer program product and computer system for object detection and identification. The method, computer program product and computer system may include computing device which may receive an image from an imaging device. The image may be a medical image. The computing device may detect one or more potential indicators of disease in the image using a first algorithm and determine areas of potential disease in the image using an artificial intelligence algorithm. The computing device may determine a correlation between the determined areas of potential disease in the image and the one or more potential indicators of disease for the image. The computing device may, in response to determining a positive correlation, identify one or more of the potential indicators of disease for annotation and generate a report indicating one or more potential indicators of disease was found in the image.

BRIEF DESCRIPTION OF THE DRAWINGS

FIG. 1b illustrates example operating modules of the image annotation program of FIG. 1a.

FIG. 1c illustrates an example marked image generated by the image annotation program of FIG. 1a.

FIG. 1d illustrates an example heat map generated by the image annotation program of FIG. 1a.

DETAILED DESCRIPTION

Figure 1A:
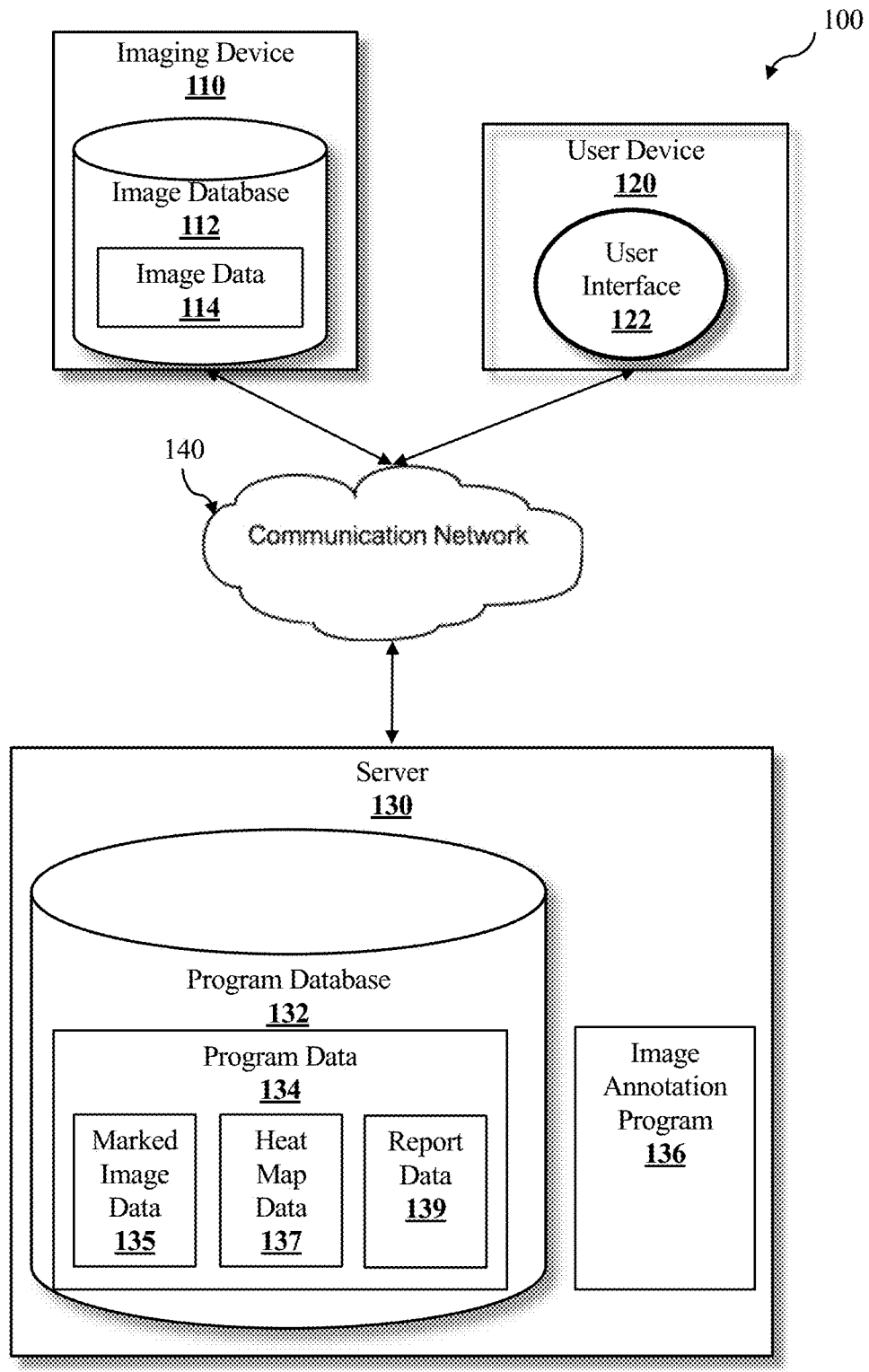
FIG. 1a illustrates a system for image analysis and annotation, in accordance with an embodiment of the invention.

Embodiments of the present invention will now be described in detail with reference to the accompanying Figures.

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments of the present invention provide a method, computer program, and computer system for analyzing medical images for disease and disease probability and annotating the medical images. Artificial Intelligence (AI) can be trained on diagnostic patient images to distinguish those that are normal from others (such as unknown or abnormal). However, one of the challenges is the cost to train AI algorithms to explicitly report benign findings as there can be a lot of benign findings. Further, training an AI system to automatically detect benign findings and other findings can be challenging as the AI systems cannot tell a person exactly what was found in understandable terms. One of the challenges is that deep learning systems can be trained to distinguish between different types of images/diagnoses without explicitly locating the same types of intermediary findings we humans rely on. AI systems encode information in different ways than humans but they may achieve the same outcomes (for example cancer detection). For example, an AI system may encode a combination of shape and texture information into a deep layer that cannot be interpreted by a human.

In many cases it is important for the AI system to show humans how it came to its conclusion. Embodiments of the present invention generate annotated reports based on the CAD algorithms and probability findings. This could be for regulatory approval of the AI Algorithm or during clinical practice. One example is in women's breast imaging for cancer screening. BI-RADS (R) is a lexicon established by the American College of Radiologists that is used to categorize different types of lesions. Normal images can be either BI-RADS 1 or BI-RADS 2 where BI-RADS 1 is a Normal imaging study with no significant image findings and BI-RADS 2 is a Normal study with benign findings. Benign findings are for example benign calcifications or benign cysts that are not problematic but get noted in the report. Approximately 80% of women have some form of benign findings within their screening X-ray mammogram. Although it is possible to train an AI algorithm to detect all these findings it is cost-prohibitive to train an AI algorithm on such large numbers of different types of benign findings. Embodiments of the present invention aim to improve the way AI algorithms report on image findings by pairing the AI algorithms with CAD algorithms to rule out and any benign findings thus allowing the system to focus on potential indicators of disease.

Embodiments of the invention include determining the probability of disease through AI by identifying areas of a medical image that should be annotated and noted in an automatically generated Report. A Computer Aided Detection (CAD) algorithm is run on an image to identify all potential indicators based on image-based features doctors are familiar with for example as described in the ACR BI-RADS® lexicon. CAD markers are well known in Radiology; however, they can have a significant rate of false-positives which has caused Radiologists to stop using CAD. In embodiments of the present invention, AI may be used to reduce those false-positives when generating medical reports by generating a heat map and/or applying probabilities to select which findings should go into the report. For example, embodiments of the present invention may use AI to assess whether CAD Findings should appear in a medical report. Embodiments of the present invention may use the AI-generated heat map to identify which CAD Findings may be automatically annotated in the image and/or noted in the report. The rationale behind the embodiments of the invention is the deep learning AI encodes information that humans cannot comprehend. By cross-correlating a heat map generated by an AI algorithm with CAD markers generated by a CAD algorithm, a system, according to various embodiments, automatically identifies which CAD findings should be annotated, i.e. summarized, and added to the medical report. CAD algorithms are designed to identify features that doctors are familiar with, for example ACR BI-RADS® lexicon.

Reference will now be made in detail to the embodiments of the present invention, examples of which are illustrated in the accompanying drawings, wherein like reference numerals refer to like elements throughout. Embodiments of the invention are generally directed to a system for image analysis and annotation.

FIG. 1 illustrates an image analysis and annotation system 100, in accordance with an embodiment of the invention. In an example embodiment, object detection and identification system 100 includes an image device 110, a user device 120, and server 130, interconnected via network 140.

In the example embodiment, the network 140 is the Internet, representing a worldwide collection of networks and gateways to support communications between devices connected to the Internet. The network 140 may include, for example, wired, wireless or fiber optic connections. In other embodiments, the network 140 may be implemented as an intranet, a local area network (LAN), or a wide area network (WAN). In general, the network 140 can be any combination of connections and protocols that will support communications between the image device 110, the user device 120, and the server 130.

The image device 110 may include the image database 112. The image device 110 may be any device capable of capturing the image data 114. The image data 114 may include, but is not limited to, visual, audio, and/or textual data. In an example embodiment, the image device 110 may be a medical imaging device such as, but not limited to, X-ray radiography, magnetic resonance imaging (MRI), medical ultrasonography or ultrasound, endoscopy, elastography, tactile imaging, thermography, medical photography, photoacoustic imaging, electrocardiography, functional near-infrared spectroscopy (FNIR), magnetic particle imaging (MPI), and nuclear medicine functional imaging techniques as positron emission tomography (PET) and Single-photon emission computed tomography (SPECT) or any other imaging device capable of capturing the image data 114 and sending the image data 114 to and from other computing devices, such as the user device 120, and the server 130 via the network 140. The image data 114 may include any images captured by the imaging device 110 such as, but not limited to, X-rays, magnetic resonance images (MRIs), ultrasounds, endoscopic images, elastography images, tactile images, thermography images, medical photographs, photoacoustic images, electrocardiographs, functional neuroimages, magnetic particle imaged (MPIs), positron emission tomography (PET) scans, and Single-photon emission computed tomography (SPECT) scans. Further, the image data 114 may include data identifying the source of the image data 114 such as, but not limited to, patient name, patient age, patient sex, patient medical history, area of imaging, date of imaging, location of imaging, etc. The image device 110 is described in more detail with reference to FIG. 3.

The image database 112 may store the image data 114, i.e. the visual, audio, and/or textual data, captured by the image device 110. The image database 112 may be any storage media capable of storing data capable of storing data, such as, but not limited to, storage media resident in the image device 110 and/or removeable storage media. For example, the image database 112 may be, but is not limited to, a hard drive, a solid stated drive, a USB drive, or a memory card, etc. The image database 112 is described in more detail above and with reference to FIG. 3.

The user device 120 may include the user interface 122. In the example embodiment, the user device 120 may be a cellphone, desktop computer, a notebook, a laptop computer, a tablet computer, a thin client, or any other electronic device or computing system capable of storing compiling and organizing audio, visual, or textual content and receiving and sending that content to and from other computing devices, such as the image device 110, and the server 130 via the network 140. While only a single user device 120 is depicted, it can be appreciated that any number of user devices may be part of the image analysis and annotation system 100. In embodiments of the invention, the image device 110 and the user device 120 may be the same device. For example, a medical imaging device may have a computer incorporated into the device or be resident in a computer. The user device 120 is described in more detail with reference to FIG. 3.

The user interface 122 includes components used to receive input from a user on the user device 120 and transmit the input to the image annotation program 136 residing on server 130, or conversely to receive information from the image annotation program 136 and display the information to the user on user device 120. In an example embodiment, the user interface 122 uses a combination of technologies and devices, such as device drivers, to provide a platform to enable users of the user device 120 to interact with the image annotation program 136. In an example embodiment, the user interface 122 receives input, such as but not limited to, textual, visual, or audio input received from a physical input device, such as but not limited to, a keypad and/or a microphone.

The server 130 may include the program database 132 and the image annotation program 136. In the example embodiment, the server 130 may be a desktop computer, a notebook, a laptop computer, a tablet computer, a thin client, or any other electronic device or computing system capable of storing compiling and organizing audio, visual, or textual content and receiving and sending that content to and from other computing devices, such as the image device 110, and the user device 120 via network 140. In some embodiments, the server 130 includes a collection of devices, or data sources, in order to collect the program data 134. The server 130 is described in more detail with reference to FIG. 3.

The program database 132 may store the program data 134. The program database 132 may be any storage media capable of storing data capable of storing data, such as, but not limited to, storage media resident in the server 130 and/or removeable storage media. For example, the program database 132 may be, but is not limited to, a hard drive, a solid stated drive, a USB drive, or a memory card, etc. The program database 132 is described in more detail below and with reference to FIG. 3.

The program data 134 may be a collection of audiovisual content required by the image annotation program 136 including, but not limited to, audio, visual, and textual content. The program data 134 may be, for example, but not limited to, the image data 114 received and/or collected from the image device 110 and the user device 120, the marked image 135 generated by the image annotation program 136, the heat map 137 generated by the image annotation program 136, and/or the report data 139 generated by the image annotation program 136. The marked image 135, the heat map 137, and the report data 139 are described in more detail below with reference to FIGS. 1b, 1c, 1d, 2, and 3. Further, the program data 134 may include, but is not limited to, user data, patient data, imaging studies, and medical reports, etc. The program data 134 is located on the server 130 and can be accessed via the network 140. In accordance with an embodiment of the invention, the program data 134 may be located on one or a plurality of servers 130.

The image annotation program 136 is a program capable of receiving the image data 114 captured by the image device 110 and analyzing the image data 114 to determine the probability the image data 114 indicates disease and to annotate the image data 114. Further, the image annotation program 136 may generate a report including the disease annotations and determinations. The image annotation program 136 is described in more detail below with reference to FIG. 1b.

Figure 1B:
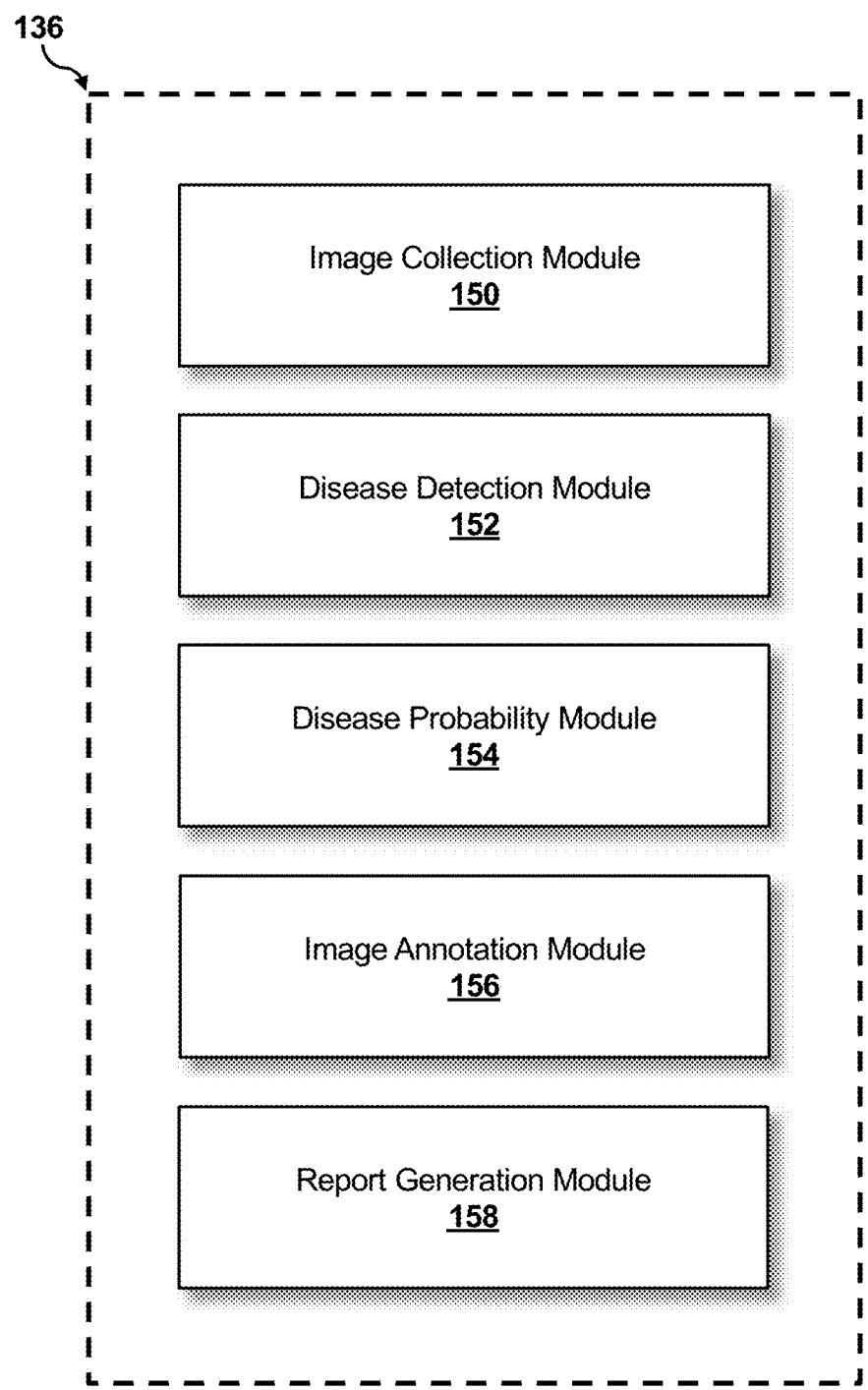

FIG. 1b illustrates example modules of the image annotation program 136. In an example embodiment, the image annotation program 136 may include five modules: image collection module 150, disease detection module 152, disease probability module 154, image annotation module 156, and report generation module 158.

The image collection module 150 receives the image data 114 captured from the image device 110 by the user device 120 and/or directly from the image device 110. For example, but not limited to, the user device 120 may collect a medical image from the image device 110 using the user interface 122. The medical image would then be sent to the server 130 via the user interface 122 over the network 140 where it would be received by the image capture module 150 of the image annotation program 136. In an embodiment of the invention, the image data 114 may be stored in the program data 134 on the program database 132.

The disease detection module 152 analyzes the image data 114 to detect if there are any potential indicators of disease contained within the image data 114. For example, but not limited to, the disease detection module 152 may analyze a CAT scan to detect if the CAT scan contains any indicators of cancer, such as a tumor. The disease detection module 152 may utilize a Computer Aided Detection (CAD or CADe) algorithm. CAD or CADe algorithms are image-based algorithms that can automatically detect a feature within a medical image such as, but not limited to, a cancer lesion in the breast or the lung. Further, the disease detection module 152 may mark the image data 114 with markings 160 indicating potential indicators of disease to generate the marked image 135, as illustrate in FIG. 1c. The markings 160 on the marked image 135 may be, but are not limited to, CAD markings.

Figure 1C:
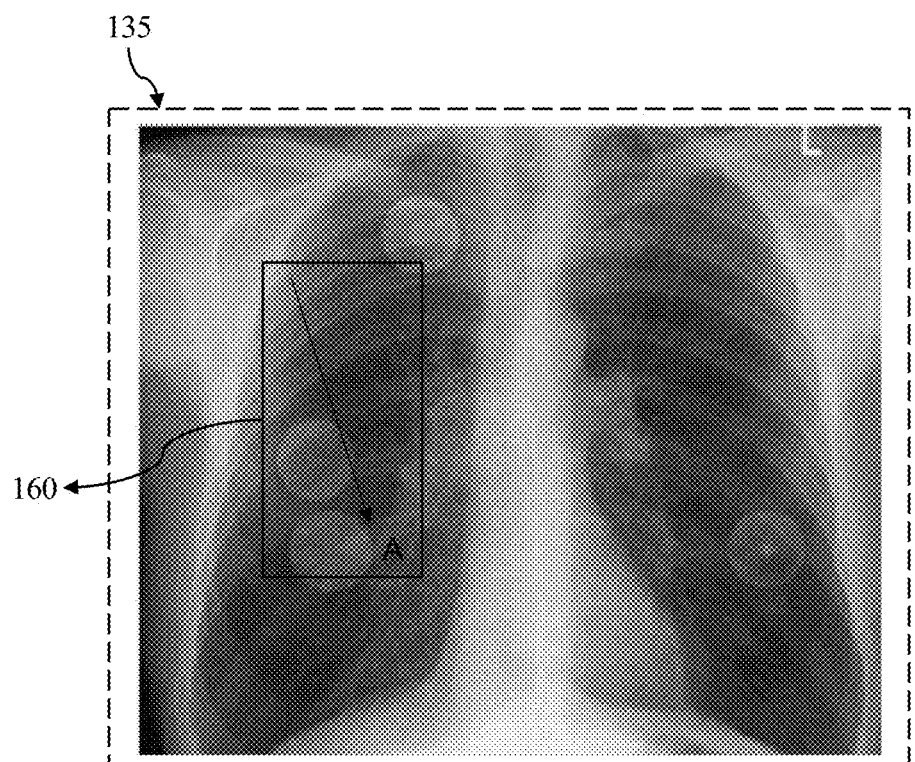
Figure 1D:
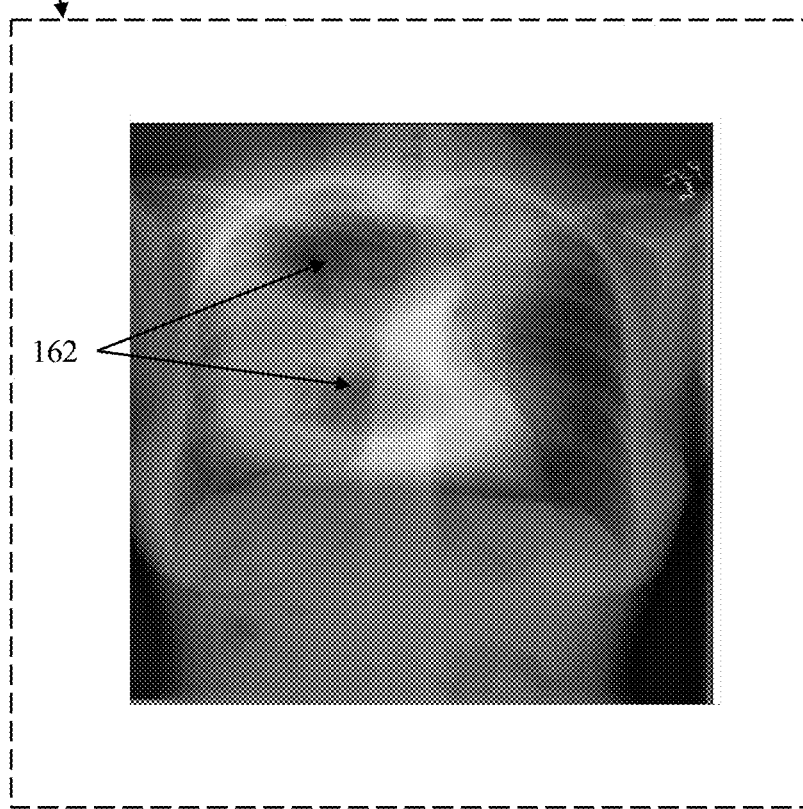

The disease probability module 154 determines the areas 162 of potential disease. The disease probability module 154 may generate a disease probability map, such as, but not limited to, a heat map, and/or a spatial map, etc. of the areas 162 contained within the image data 114 that may be potential indicators of disease. The disease probability module 154 may determine the areas 162 of potential disease for example, but not limited to, by generating a heat map 137 indicating the areas 162 of potential abnormalities in the image data 114. For example, disease probability module 154 may generate a heat map 137 for a medical image, e.g. an X-ray image, indicating the areas 162 of the medical image which may indicate disease, e.g. cancer lesions as illustrated in FIG. 1d. The areas 162 may be indicated using for example, but not limited to, numerical values, shading, and/or coloring, etc. The disease probability module 154 may generate the heat map 137 using artificial intelligence (AI), such as, but not limited to a deep learning. Deep learning allows software, such as image annotation program 136, learn to recognize patterns in distinct layers using one or more neural networks which operate both independently and in concert, separating aspects such as color, size and shape before integrating the outcomes. Deep learning may utilize one or more deep neural networks such as, but not limited to, convolutional deep neural networks (CNNs). Deep convolutional neural networks are a class of deep, feed-forward artificial neural networks consisting of an input layer, an output layer, and multiple hidden layers used to analyze images. Further, the disease probability module 154 may generate the heat map 137 using the object recognition technology such as, but not limited to, a saliency detection algorithm such as SalNet. SalNet is a deep learning algorithm which automatically detects salients for a given image such as the image data 114. The saliency of an image is the state or quality by which it stands out relative to its neighbors, i.e. localizing what people see when they view the image. Saliency detection is considered to be a key attentional mechanism that facilitates learning and survival by enabling organisms to focus their limited perceptual and cognitive resources on the most pertinent subset of the available sensory data. Saliency detection stresses on four types of features, namely color, luminance, texture, and depth. In embodiments of the present invention, saliency detection concentrates primarily on static saliency and objectness. Static saliency detection algorithms use different image features that allow detecting salient object of a non-dynamic image and objectness estimation seeks to propose a small set of bounding boxes according to the possibility of a complete object existing around a region. Thus, the disease probability module 154 may utilize a saliency detection algorithm to determine the areas 162 contained within the image data 114 that may be potential indicators of disease.

The image annotation module 156 identifies which potential indicators of disease contained in the image data 114 to annotate. Image annotation is described in more detail below with reference to the report generation module 158. The image annotation module 156 correlates the potential indicators of disease detected by the disease detection module 152 and the disease probability map generated by the disease probability module 154. The image annotation module 156 may correlate the potential indicators of disease detected by the disease detection module 152 and the disease probability map, e.g. a heat map, generated by the disease probability module 154 by comparing the location of the potential indicators of disease with the areas indicating potential abnormalities in the heat map. Thus, if the location of one or more potential indicators of disease are located within the areas indicating potential abnormalities in the heat map, the image annotation module 156 may determine that those one or more potential indicators of disease within the areas indicating potential abnormalities in the heat map indicate disease, i.e. there is a positive correlation. If the location of one or more potential indicators of disease are not located within the areas indicating potential abnormalities in the heat map, the image annotation module 156 may determine that those one or more potential indicators of disease locate outside the areas indicating potential abnormalities in the heat map do no indicate disease, i.e. there is a negative correlation. In other embodiments, the correlation between the potential indicators of disease, e.g. the CAD markings, and the disease probability map, e.g. a heat map, may result in a correlation coefficient, i.e. a threshold, which the image annotation module 156 may use to determine which potential indicators of disease to annotate. For example, if the correlation coefficient is positive, i.e. greater than 0, the image annotation module 156 may determine that the potential disease indicator associated with that correlation coefficient should be annotated and if the correlation coefficient is negative, e.g. below 0, the image annotation module 156 may determine that the potential disease indicator associated with that correlation coefficient should not be annotated. Further, it can be appreciated that the image annotation module 156 may also contain rules for varying levels of positive and negative correlation. For example, if the correlation coefficient is strong positive, e.g. between 0.5 and 1, the image annotation module 156 may determine that the potential disease indicator associated with that correlation coefficient should be annotated, but if the correlation coefficient is weak positive, e.g. between 0 and 0.5, the image annotation module 156 may determine that further review is required. The further review may include, but is not limited to, running the image data 114 through the image annotation program 136 again, and/or review by a doctor or medical imaging technician.

The report generation module 158 generates a report based on the output of the image annotation module 156. The report may be a natural language report generated using natural language processing (NLP). For example, the report generation module 158 may generate a report stating that the image data 114, e.g. a mammogram, contains an area which indicates a high probability of breast cancer. The report may include the image data 114 with the markings 160 and/or the heat map 137 determined by the disease detection module 152 and/or the disease probability module 154, such as, but not limited to, the image data 114 as illustrated in FIGS. 1c-1d. Further, the report generation module 158 may include recommendations based on the probabilities, i.e. correlations, determined by the image annotation program 136. For example, but not limited to, if the image annotation program 136 determines that the image data 114 falls within a certain range the image data 114 should be reviewed further to confirm the findings.

Figure 2:
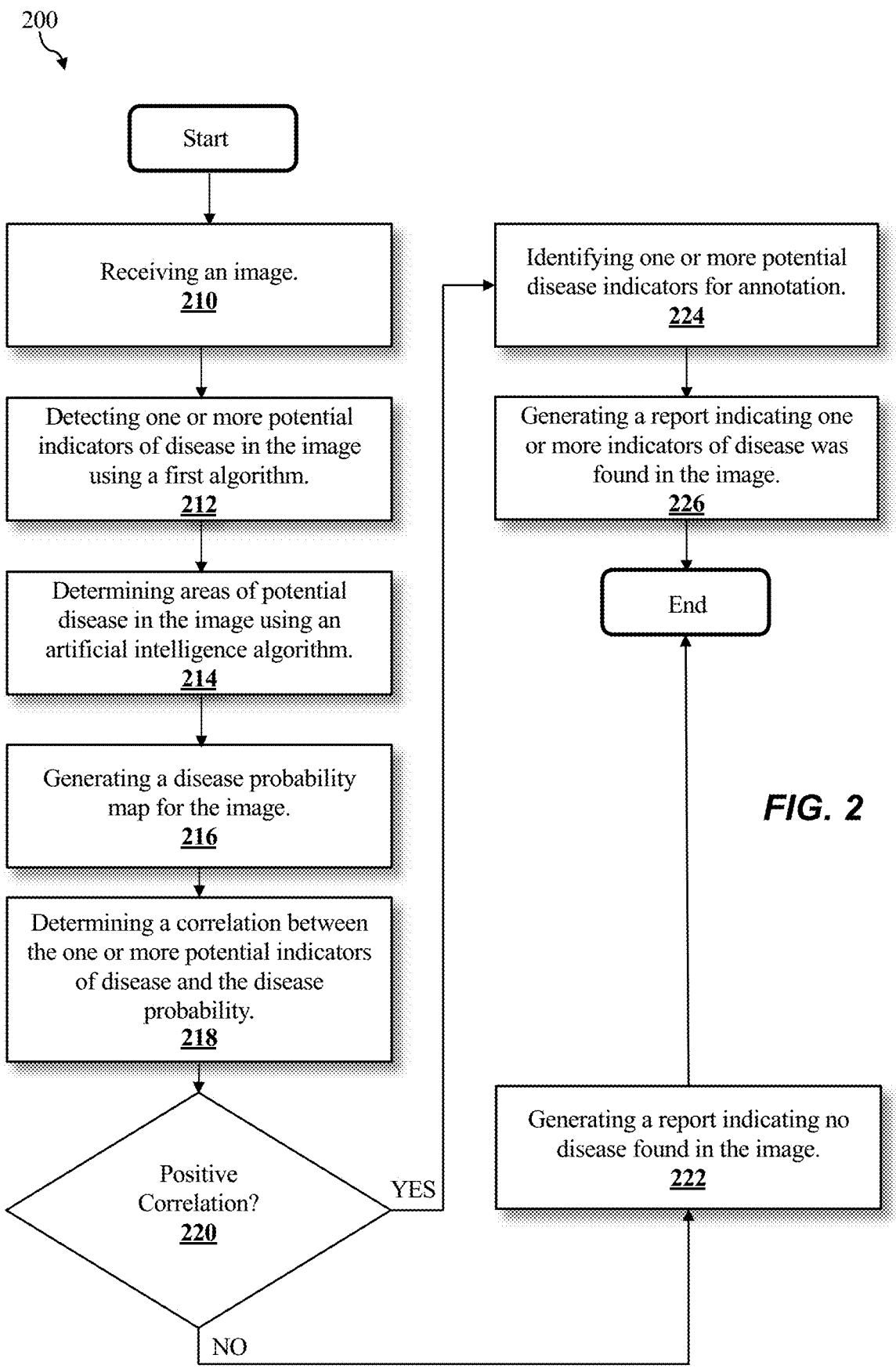
FIG. 2 is a flowchart illustrating an example method of image analysis and annotation in accordance with an embodiment of the invention.

Referring to FIG. 2, a method 200 for image analysis and annotation is depicted in accordance with an embodiment of the present invention.

Referring to block 210, the image collection module 150 receives the image data 114 captured from the image device 110 by the user device 120 and/or directly from the image device 110. Image collection is described in more detail above with reference to the image collection module 150 of FIG. 1b.

Referring to block 212, the disease detection module 152 analyzes the image data 114 to detect if there are any potential indicators of disease contained within the image data 114. Disease detection is described in more detail above with reference to the disease detection module 152 of FIG. 1b.

Referring to block 214, the disease probability module 154 determines areas of potential disease in the image data 114. Disease probability determination is described in more detail above with reference to the disease probability module 154 of FIG. 1b.

Referring to block 216, the disease probability module 154 generates a disease probability map for the image data 114. Disease probability map generation is described in more detail above with reference to the disease probability module 154 of FIG. 1b.

Referring to block 218, the image annotation module 156 correlates the potential indicators of disease detected by the disease detection module 152 and the areas of potential disease determined by the disease probability module 154. Disease probability correlation is described in more detail above with reference to the image annotation module 156 of FIG. 1b.

Referring to block 220, the image annotation module 156 determines if there is a positive correlation between the potential indicators of disease detected by the disease detection module 152 the areas of potential disease determined by the disease probability module 154. If the image annotation module 156 determines a negative correlation, the image annotation program 136 proceeds to block 222. If the image annotation module 156 determines a positive correlation, the image annotation program 136 proceeds to block 224. Correlation determination is described in more detail above with reference to the image annotation module 156 of FIG. 1b.

Referring to block 222, the report generation module 158 generates a report indicating that no disease was found in the image data 114. Report generation is described in more detail above with reference to the report generation module 158 of FIG. 1b.

Referring to block 224, the image annotation module 156 identifies which potential indicators of disease to annotate. Annotation determination is described in more detail above with reference to image annotation module 156 of FIG. 1b.

Referring to block 226, the report generation module 158 generates a report indicating one or more indicators of disease was found in the image data 114. Report generation is described in more detail above with reference to the report generation module 158 of FIG. 1b.

Referring to FIG. 2, a method 300 for image analysis and annotation is depicted in accordance with an embodiment of the present invention. Blocks 310-318 of the method 300 are the same as block 210-218 of the method 200, respectively.

Referring to block 320, the image annotation module 156 determines a discrepancy between the disease probability map and the detected one or more potential indicators of disease. Image discrepancy is de is described in more detail above with reference to image annotation module 156 of FIG. 1b.

Referring to block 322, the report generation module 158 generates a report indicating further review of the image data 114 is required. Report generation is described in more detail above with reference to the report generation module 158 of FIG. 1b.

Figure 3:
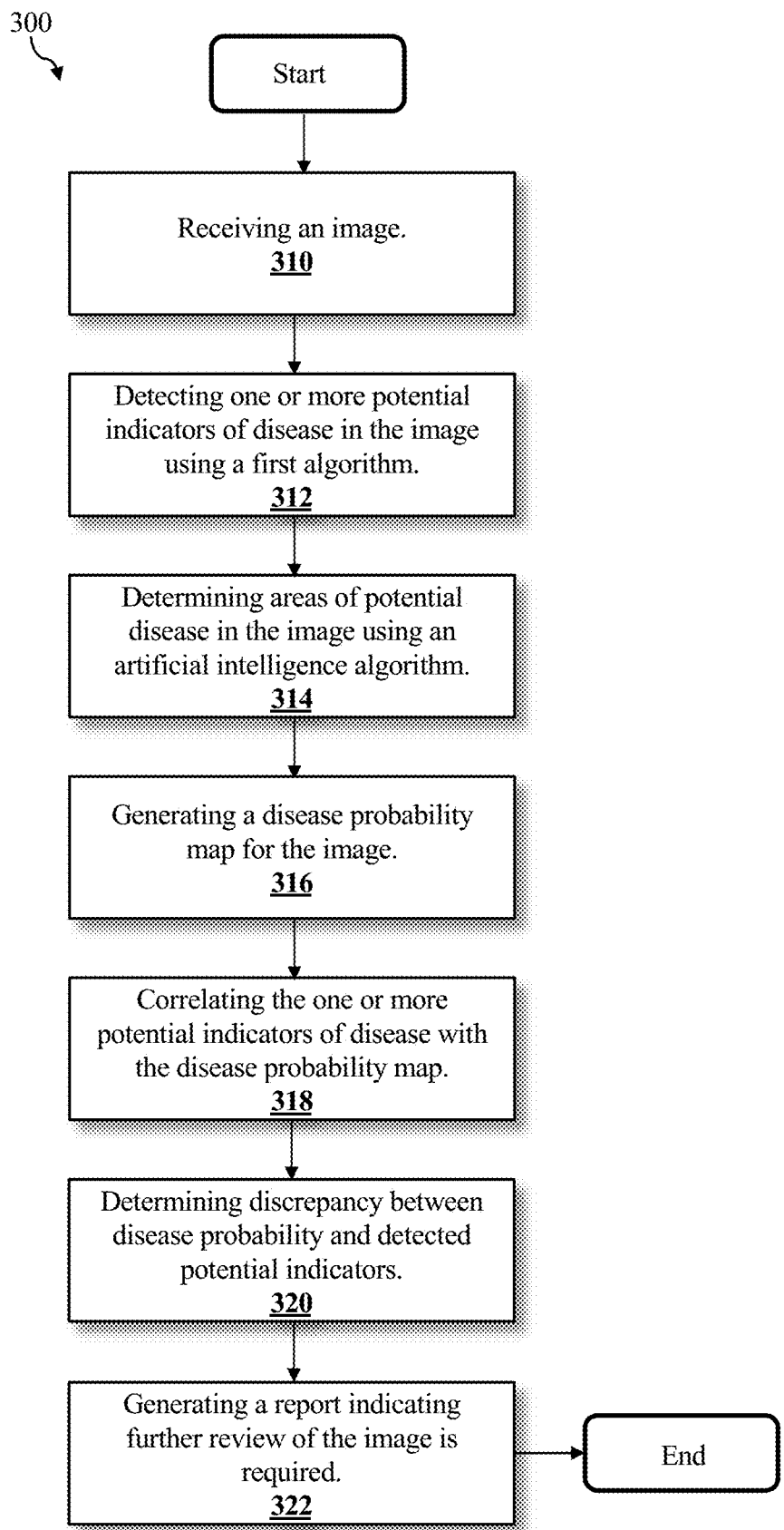
FIG. 3 is a flowchart illustrating an example method of image analysis and annotation in accordance with an embodiment of the invention.
Figure 4:
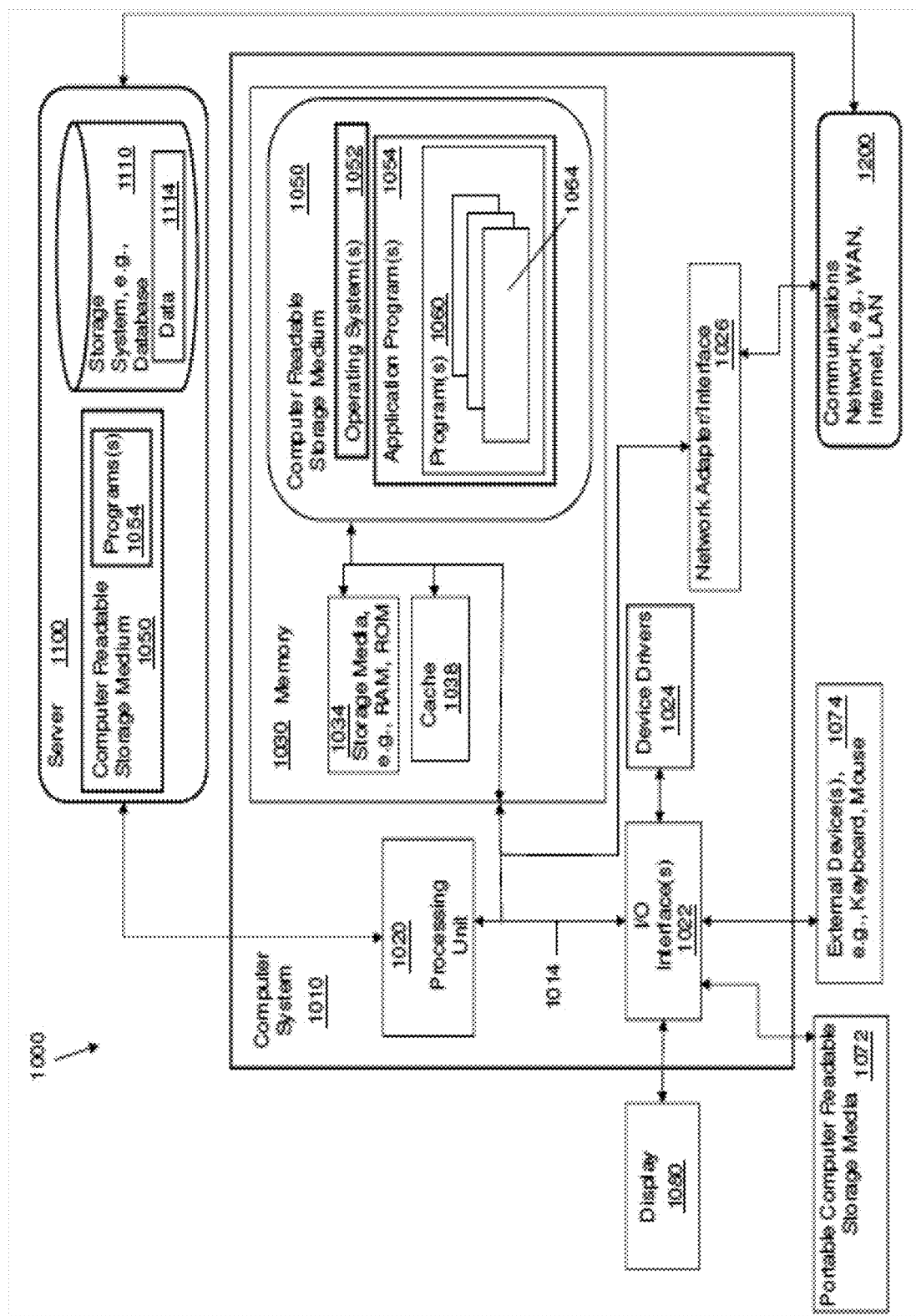
FIG. 4 is a block diagram depicting the hardware components of the image analysis and annotation system of FIG. 1, in accordance with an embodiment of the invention.

Referring to FIG. 4, a system 1000 includes a computer system or computer 1010 shown in the form of a generic computing device. The methods 200 and 300 for example, may be embodied in a program(s) 1060 (FIG. 4) embodied on a computer readable storage device, for example, generally referred to as memory 1030 and more specifically, computer readable storage medium 1050 as shown in FIG. 4. For example, memory 1030 can include storage media 1034 such as RAM (Random Access Memory) or ROM (Read Only Memory), and cache memory 1038. The program 1060 is executable by the processing unit or processor 1020 of the computer system 1010 (to execute program steps, code, or program code). Additional data storage may also be embodied as a database 1110 which can include data 1114. The computer system 1010 and the program 1060 shown in FIG. 3 are generic representations of a computer and program that may be local to a user, or provided as a remote service (for example, as a cloud based service), and may be provided in further examples, using a website accessible using the communications network 1200 (e.g., interacting with a network, the Internet, or cloud services). It is understood that the computer system 1010 also generically represents herein a computer device or a computer included in a device, such as a laptop or desktop computer, etc., or one or more servers, alone or as part of a datacenter. The computer system can include a network adapter/interface 1026, and an input/output (I/O) interface(s) 1022. The I/O interface 1022 allows for input and output of data with an external device 1074 that may be connected to the computer system. The network adapter/interface 1026 may provide communications between the computer system a network generically shown as the communications network 1200.

The computer 1010 may be described in the general context of computer system-executable instructions, such as program modules, being executed by a computer system. Generally, program modules may include routines, programs, objects, components, logic, data structures, and so on that perform particular tasks or implement particular abstract data types. The method steps and system components and techniques may be embodied in modules of the program 1060 for performing the tasks of each of the steps of the method and system. The modules are generically represented in FIG. 4 as program modules 1064. The program 1060 and program modules 1064 can execute specific steps, routines, sub-routines, instructions or code, of the program.

The methods of the present disclosure can be run locally on a device such as a mobile device, or can be run a service, for instance, on the server 1100 which may be remote and can be accessed using the communications network 1200. The program or executable instructions may also be offered as a service by a provider. The computer 1010 may be practiced in a distributed cloud computing environment where tasks are performed by remote processing devices that are linked through a communications network 1200. In a distributed cloud computing environment, program modules may be located in both local and remote computer system storage media including memory storage devices.

More specifically, as shown in FIG. 4, the system 1000 includes the computer system 1010 shown in the form of a general-purpose computing device with illustrative periphery devices. The components of the computer system 1010 may include, but are not limited to, one or more processors or processing units 1020, a system memory 1030, and a bus 1014 that couples various system components including system memory 1030 to processor 1020.

The bus 1014 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer 1010 can include a variety of computer readable media. Such media may be any available media that is accessible by the computer 1010 (e.g., computer system, or server), and can include both volatile and non-volatile media, as well as, removable and non-removable media. Computer memory 1030 can include additional computer readable media 1034 in the form of volatile memory, such as random access memory (RAM), and/or cache memory 1038. The computer 1010 may further include other removable/non-removable, volatile/non-volatile computer storage media, in one example, portable computer readable storage media 1072. In one embodiment, the computer readable storage medium 1050 can be provided for reading from and writing to a non-removable, non-volatile magnetic media. The computer readable storage medium 1050 can be embodied, for example, as a hard drive. Additional memory and data storage can be provided, for example, as the storage system 1110 (e.g., a database) for storing data 1114 and communicating with the processing unit 1020. The database can be stored on or be part of a server 1100. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1014 by one or more data media interfaces. As will be further depicted and described below, memory 1030 may include at least one program product which can include one or more program modules that are configured to carry out the functions of embodiments of the present invention. As such, the computing device in FIG. 4 becomes specifically configured to implement mechanisms of the illustrative embodiments and specifically configured to perform the operations and generated the outputs of described herein for determining a route based on a user's preferred environmental experiences.

The methods 200 and 300 (FIGS. 2 and 3), for example, may be embodied in one or more computer programs, generically referred to as a program(s) 1060 and can be stored in memory 1030 in the computer readable storage medium 1050. The program 1060 can include program modules 1064. The program modules 1064 can generally carry out functions and/or methodologies of embodiments of the invention as described herein. For example, the program modules 1064 can include the modules 150-158 described above with reference to FIG. 1b. The one or more programs 1060 are stored in memory 1030 and are executable by the processing unit 1020. By way of example, the memory 1030 may store an operating system 1052, one or more application programs 1054, other program modules, and program data on the computer readable storage medium 1050. It is understood that the program 1060, and the operating system 1052 and the application program(s) 1054 stored on the computer readable storage medium 1050 are similarly executable by the processing unit 1020.

The computer 1010 may also communicate with one or more external devices 1074 such as a keyboard, a pointing device, a display 1080, etc.; one or more devices that enable a user to interact with the computer 1010; and/or any devices (e.g., network card, modem, etc.) that enables the computer 1010 to communicate with one or more other computing devices. Such communication can occur via the Input/Output (I/O) interfaces 1022. Still yet, the computer 1010 can communicate with one or more networks 1200 such as a local area network (LAN), a general wide area network (WAN), and/or a public network (e.g., the Internet) via network adapter/interface 1026. As depicted, network adapter 1026 communicates with the other components of the computer 1010 via bus 1014. It should be understood that although not shown, other hardware and/or software components could be used in conjunction with the computer 1010. Examples, include, but are not limited to: microcode, device drivers 1024, redundant processing units, external disk drive arrays, RAID systems, tape drives, and data archival storage systems, etc.

It is understood that a computer or a program running on the computer 1010 may communicate with a server, embodied as the server 1100, via one or more communications networks, embodied as the communications network 1200. The communications network 1200 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer 1010, including a mobile device, can use a communications system or network 1200 which can include the Internet, or a public switched telephone network (PSTN) for example, a cellular network. The PSTN may include telephone lines, fiber optic cables, microwave transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
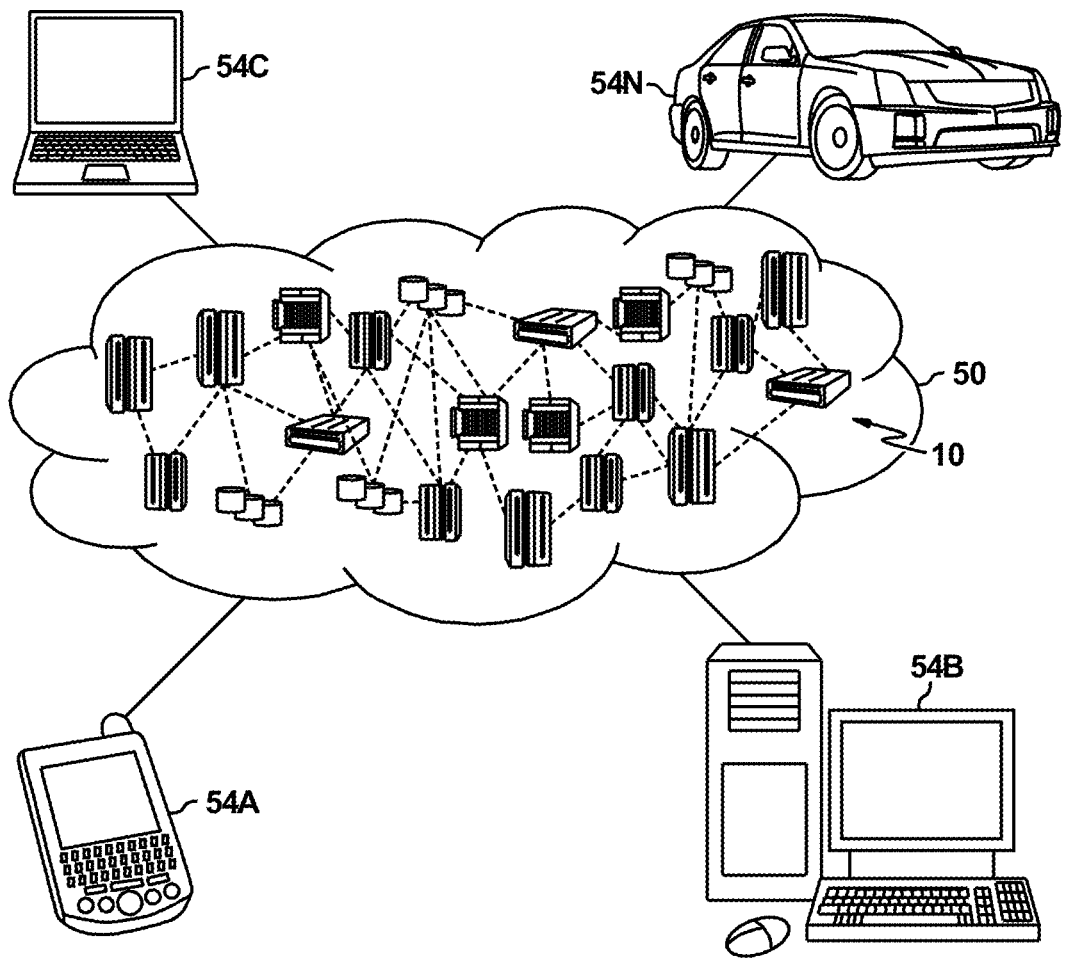
FIG. 5 illustrates a cloud computing environment, in accordance with an embodiment of the invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
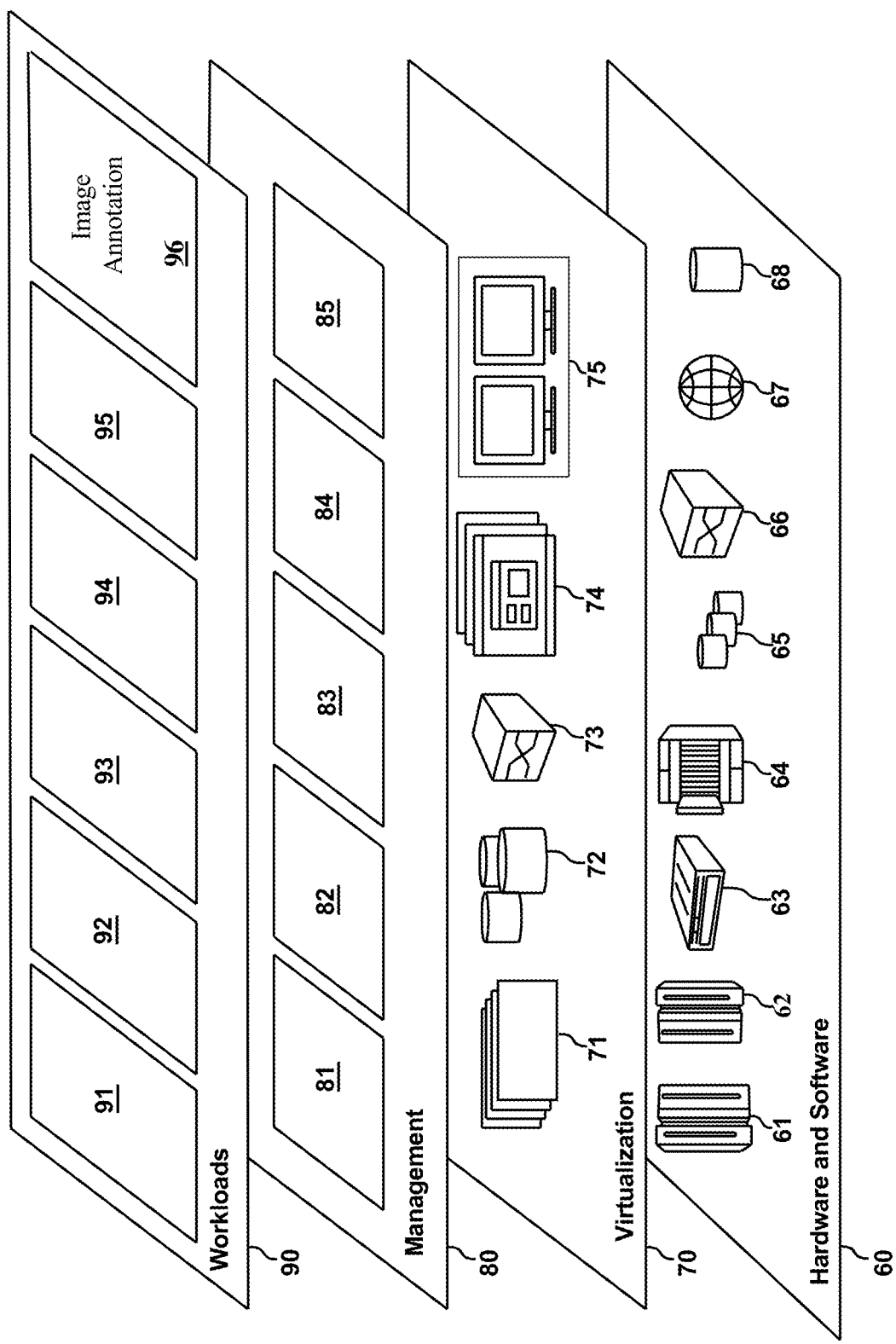
FIG. 6 illustrates a set of functional abstraction layers provided by the cloud computing environment of FIG. 5, in accordance with an embodiment of the invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and image annotation 96.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

What is claimed is:

1. A method for improving image analysis and annotation, the method comprising:
   receiving, by a computing device, an image from an imaging device, wherein the image is a medical image;
   detecting, by the computing device, one or more potential indicators of disease in the image using a Computer Aided Detection algorithm;
   determining, by the computing device, a disease probability map having areas of potential disease in the image using an artificial intelligence algorithm, wherein the artificial intelligence algorithm is a deep learning algorithm that detects one or more salients in the image and generates the disease probability map;
   determining, by the computing device, a positive correlation between the determined areas of potential disease in the image and the one or more potential indicators of disease for the image, wherein the positive correlation is determined when the one or more potential indicators of the disease is within the disease probability map;
   reducing false-positives by generating a heat map based on the areas of potential disease in the image;
   identifying one or more findings by cross-correlating the heat map and the one or more potential indicators of disease in the image using the Computer Aided Detection algorithm; and generating, using a natural language processing, a report in a natural language that includes recommendations for the one or more findings based on the disease probability map.

2. The method as in claim 1, further comprising:
in response to determining the positive correlation, identifying, by the computing device, one or more of the potential indicators of disease for annotation; and
generating, by the computing device, the report indicating one or more potential indicators of disease was found in the image.

3. The method as in claim 1, further comprising:
in response to determining a negative, generating, by the computing device, the report indicating no potential indicators of disease were found in the image.

4. The method as in claim 1, further comprising:
determining, by the computing device, a discrepancy between the areas of potential disease and the one or more potential indicators of disease; and
generating, by the computing device, the report indicating further review of the image is required.

5. The method as in claim 1, wherein the one or more potential indicators of disease in the image are further detected using a computer aided detection algorithm, the computer aided detection algorithm generating markings for the one or more potential indicators of disease on the image.

6. The method as in claim 1, wherein the areas of potential disease in the image are determined using a saliency detection algorithm.

7. A computer program product for improving image analysis and annotation, the computer program product comprising:
a computer-readable storage medium having program instructions embodied therewith, wherein the computer readable storage medium is not a transitory signal per se, the program instructions comprising:
program instructions to receive, by a computing device, an image from an imaging device, wherein the image is a medical image;
program instructions to detect, by the computing device, one or more potential indicators of disease in the image using a Computer Aided Detection algorithm;
program instructions to determine, by the computing device, a disease probability map having areas of potential disease in the image using an artificial intelligence algorithm, wherein the artificial intelligence algorithm is a deep learning algorithm that detects one or more salients in the image and generates the disease probability map;
program instructions to determine, by the computing device, a positive correlation between the determined areas of potential disease in the image and the one or more potential indicators of disease for the image, wherein the positive correlation is determined when the one or more potential indicators of the disease is within the disease probability map;
program instructions to reduce false-positives by generating a heat map based on the areas of potential disease in the image;
program instructions to identify one or more findings by cross-correlating the heat map and the one or more potential indicators of disease in the image using the Computer Aided Detection algorithm; and
program instructions to generate, using a natural language processing, a report in a natural language that includes recommendations for the one or more findings based on the disease probability map.

8. The computer program product as in claim 7, further comprising:
in response to determining the positive correlation, program instructions to identify, by the computing device, one or more of the potential indicators of disease for annotation; and
program instructions to generate, by the computing device, the report indicating one or more potential indicators of disease was found in the image.

9. The computer program product as in claim 7, further comprising:
in response to determining a negative, program instructions to generate, by the computing device, the report indicating no potential indicators of disease were found in the image.

10. The computer program product as in claim 7, further comprising:
program instructions to determine, by the computing device, a discrepancy between the areas of potential disease and the one or more potential indicators of disease; and
program instructions to generate, by the computing device, the report indicating further review of the image is required.

11. The computer program product as in claim 7, wherein the one or more potential indicators of disease in the image are detected using a computer aided detection algorithm, the computer aided detection algorithm generating markings for the one or more potential indicators of disease on the image.

12. The computer program product as in claim 7, wherein the areas of potential disease in the image are determined using a saliency detection algorithm.

13. A computer system for improving image analysis and annotation, the system comprising:
one or more computer processors, one or more computer-readable storage media, and program instructions stored on one or more of the computer-readable storage media for execution by at least one of the one or more processors, the program instructions comprising:
program instructions to receive, by a computing device, an image from an imaging device, wherein the image is a medical image;
program instructions to detect, by the computing device, one or more potential indicators of disease in the image using a Computer Aided Detection algorithm;
program instructions to determine, by the computing device, a disease probability map having areas of potential disease in the image using an artificial intelligence algorithm, wherein the artificial intelligence algorithm is a deep learning algorithm that detects one or more salients in the image and generates the disease probability map;
program instructions to determine, by the computing device, a positive correlation between the determined areas of potential disease in the image and the one or more potential indicators of disease for the image, wherein the positive correlation is determined when the one or more potential indicators of the disease is within the disease probability map;
program instructions to reduce false-positives by generating a heat map based on the areas of potential disease in the image;
program instructions to identify one or more findings by cross-correlating the heat map and the one or more potential indicators of disease in the image using the Computer Aided Detection algorithm; and program instructions to generate, using a natural language processing, a report in a natural language that includes recommendations for the one or more findings based on the disease probability map.

14. The system as in claim 13, further comprising:
in response to determining the positive correlation, program instructions to identify, by the computing device, one or more of the potential indicators of disease for annotation; and
program instructions to generate, by the computing device, the report indicating one or more potential indicators of disease was found in the image.

15. The system as in claim 13, further comprising:
in response to determining a negative, program instructions to generate, by the computing device, the report indicating no potential indicators of disease were found in the image.

16. The system as in claim 13, further comprising:
program instructions to determine, by the computing device, a discrepancy between the areas of potential disease and the one or more potential indicators of disease; and
program instructions to generate, by the computing device, the report indicating further review of the image is required.

17. The system as in claim 13, wherein one or more potential indicators of disease in the image are detected using a computer aided detection algorithm, the computer aided detection algorithm generating markings for the one or more potential indicators of disease on the image.

* * * * *